Oct. 16, 1934. W. J. H. KORDES Plant Pat. 105
ROSE VARIETY
Filed March 23, 1934
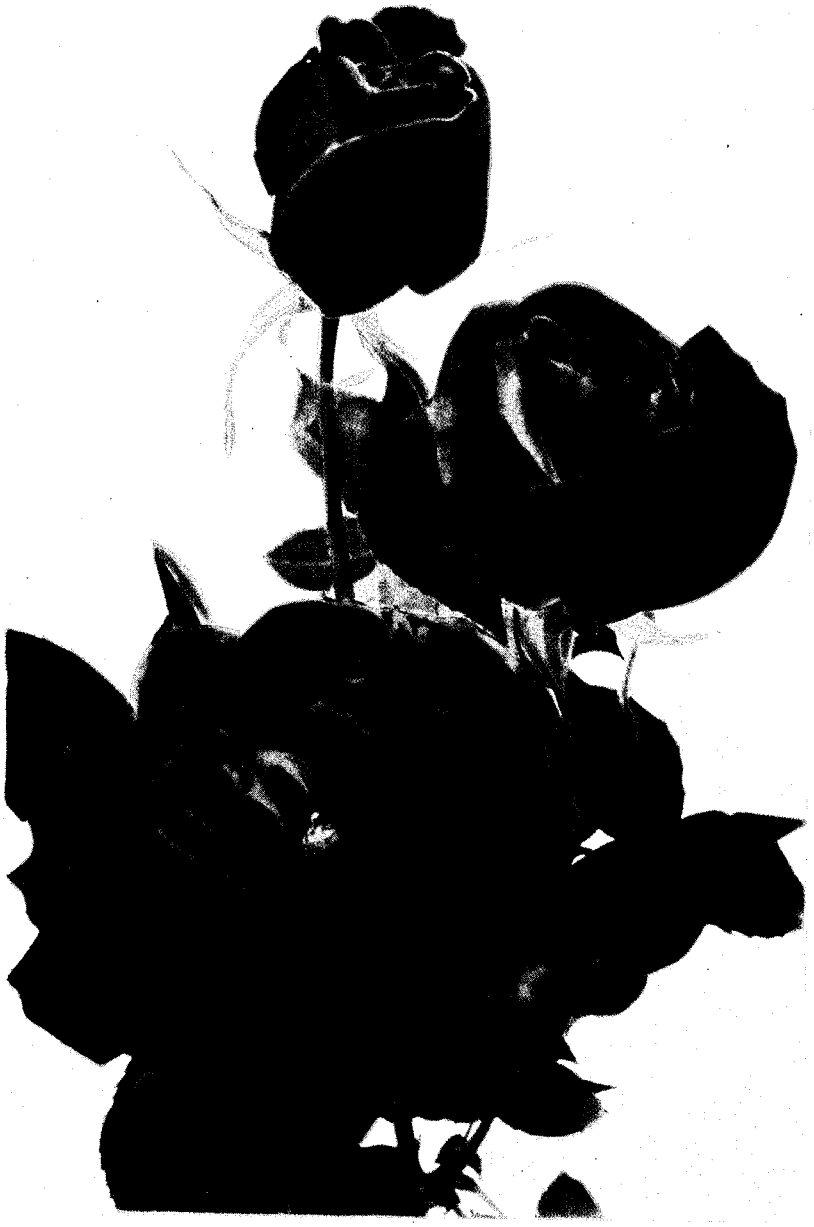
Inventor
Wilhelm John Heinrich Kordes
By Orville M. Kile
Plant Patent Agent Patented Oct. 16, 1934

UNITED STATES PATENT OFFICE

105

ROSE VARIETY

Wilhelm John Hinrich Kordes, Sparrieshoop, Germany, assignor to Henry A. Dreer, Incorporated, Philadelphia, Pa., a corporation of New Jersey Application March 23, 1934, Serial No. 717,102

1 Claim. (Cl. 47—61)

My new variety of rose belongs to the hybrid tea class. It was originated and developed by myself as a result of plant breeding efforts. This seedling first attracted my attention in 1930. This new variety is similar to Etoile de Holland in growing and blooming habits, but is much darker in color. It is particularly well adapted to outdoor use and should make a fitting companion to the well known Red Radiance.

The accompanying illustration shows in full color a bud, a partly opened flower and a fully opened flower together with foliage.

The plant is a vigorous grower having a spread, ordinarily, of 2 to 2½ feet; it is disease resistant and retains its foliage to the bottom of the plant even in late summer. This variety reproduces readily, blooms freely, is healthy and in general habits may be compared to Red Radiance.

*Stems.*—Stout, green, beset with a large number of strong, straight thorns of brownish color, set perpendicular to the stem.

*Leaves.*—On rachises 4½ to 5 inches long, ordinarily having 5 leaflets lying in the same plane. The leaflets are approximately "forest green" (Plate XVII Ridgway's Color Standard and Nomenclature), somewhat glossy, ovate, and with rather finely serrated edges. The rachis from which the leaflets spring, bears two to three small thorns pointing downward.

*Stipules.*—Moderately wide but not long, having pointed but non-curling tips.

*Hips.*—Medium sized, slightly tapering, short.

*Buds.*—Rather large and urn-shaped when opening.

*Sepals.*—Five in number, medium size, 1 to 1½ inches long, but with one to two of the sepals much longer and foliaceous in form, little or no branching.

*Blossoms.*—Petals rather velvety, large, cordate in shape, and substantial in texture. Each petal has a small white area at the point of attachment and in the case of the innermost group this white extends upward along the central line of the petal from ¼ to ½ inch, giving a striped effect. No white is visible, however, in looking at the normal blossom.

The blossoms have 22 to 24 petals in early December, with very few small central petals.

This rose has a large number of long, yellowish stamens mounted by yellowish anthers, and many white pistils with dark pink to reddish tops.

Moderately sweet scented.

The color may be popularly described as a deep velvety crimson. More technically described, the outer edges of the petals—where the high-lights fall—are approximately "carmine" (according to Ridgway's Color Standards and Nomenclature, Plate I). The deeper shades are approximately "oxblood red" (Plate I). It must be understood, however, that this color guide shows no colors that can compare with the gorgeous deep crimson nor with the many variations from this color arising from the velvety quality of the petals.

This variety has a much deeper, darker color than either the Mrs. J. D. Eisele or the Etoile de Holland.

Having thus disclosed my invention, I claim;

The variety of hybrid tea rose herein described and shown, characterized by its gorgeous deep crimson color and velvety petals combined with exceptionally vigorous growing and blooming habits, freedom from disease, and other desirable qualities.

WILHELM JOHN HINRICH KORDES.